United States Patent
Yamamoto et al.

(10) Patent No.: US 9,804,128 B2
(45) Date of Patent: Oct. 31, 2017

(54) TURBINE BLADE TESTING DEVICE AND TESTING METHOD THEREOF

(71) Applicant: Kabushiki Kaisha Toshiba, Minato-ku (JP)

(72) Inventors: Setsu Yamamoto, Yokohama (JP); Takahiro Miura, Yokohama (JP); Jun Semboshi, Yokohama (JP); Makoto Ochiai, Yokohama (JP); Masato Murakami, Yokohama (JP); Hiroshi Nomura, Machida (JP); Takuya Fuchi, Yokohama (JP)

(73) Assignee: Kabushiki Kaisha Toshiba, Minato-ku (JP)

( * ) Notice: Subject to any disclaimer, the term of this patent is extended or adjusted under 35 U.S.C. 154(b) by 424 days.

(21) Appl. No.: 14/556,346

(22) Filed: Dec. 1, 2014

(65) Prior Publication Data
US 2015/0153310 A1 Jun. 4, 2015

(30) Foreign Application Priority Data
Dec. 3, 2013 (JP) .................................. 2013-250498

(51) Int. Cl.
| | | |
|---|---|---|
| G01N 29/04 | (2006.01) | |
| G01N 29/06 | (2006.01) | |
| G01N 29/26 | (2006.01) | |
| G01N 29/28 | (2006.01) | |
| G01N 29/22 | (2006.01) | |

(52) U.S. Cl.
CPC ......... *G01N 29/04* (2013.01); *G01N 29/0645* (2013.01); *G01N 29/0654* (2013.01); *G01N 29/225* (2013.01); *G01N 29/262* (2013.01); *G01N 29/28* (2013.01); *G01N 2291/044* (2013.01); *G01N 2291/106* (2013.01); *G01N 2291/2638* (2013.01); *G01N 2291/2693* (2013.01)

(58) Field of Classification Search
CPC .... G01N 29/06; G01N 29/221; G01N 29/223; G01N 29/225; G01N 29/28; G01N 29/2493
USPC .................. 73/625, 627, 644; 376/249, 252
See application file for complete search history.

(56) References Cited

U.S. PATENT DOCUMENTS

| | | | |
|---|---|---|---|
| 7,428,842 B2 * | 9/2008 | Fair ...................... | G01N 29/262 73/602 |
| 2008/0134791 A1 * | 6/2008 | Lanken Schulz ...... | G01N 29/07 73/625 |
| 2011/0000300 A1 * | 1/2011 | Isobe ................... | G01N 29/262 73/625 |

FOREIGN PATENT DOCUMENTS

DE 3814367 A1 * 12/1988 ............. G01N 29/28

OTHER PUBLICATIONS

English machine transaltion for DE 3814367.*

* cited by examiner

*Primary Examiner* — Daniel S Larkin
*Assistant Examiner* — Anthony W Megna Fuentes
(74) *Attorney, Agent, or Firm* — Oblon, McClelland, Maier & Neustadt, L.L.P.

(57) ABSTRACT

According to one embodiment, a testing device of a turbine blade includes: a non-compressive elastic medium brought into close contact with a platform of the turbine blade in a state fastened to a turbine rotor; a probe which has piezoelectric elements arranged in an array and transmits ultrasound waves toward a fastening portion of the turbine blade through the elastic medium and receives echo waves; and a display portion for imaging an internal region of the fasten- (Continued)

ing portion on the basis of the echo waves and displaying the same.

6 Claims, 13 Drawing Sheets

TURBINE BLADE TESTING DEVICE AND TESTING METHOD THEREOF

CROSS-REFERENCE TO RELATED APPLICATIONS

This application is based upon and claims the benefit of priority from Japanese Patient application No. 2013-250498, filed on Dec. 3, 2013, the entire contents of each of which are incorporated herein by reference.

BACKGROUND OF THE INVENTION

Field of the Invention

An embodiment of the present invention relates to a testing technology of a turbine blade by an ultrasonic flaw detection test.

Description of the Related Art

An ultrasonic flaw detection test is a technology for nondestructively checking soundness of a surface and an inside of a structural material and is an indispensable testing technology in various fields.

In a phased-array ultrasonic flaw detection test (PAUT), oscillation timing (delay time) of each of a small-sized piezoelectric elements arrayed in plural is shifted, ultrasound waves having an arbitrary waveform is transmitted, and echo waves are received.

The phased-array ultrasonic flaw detection test (PAUT) can handle test targets with complicated shapes and is widely used from the view point of reduction in the number of work processes as compared with a monocular probe that can transmit ultrasound waves only at a predetermined angle.

Turbines such as large-sized power generators and the like by thermal power and nuclear power have a structure in which a base end of a rotor blade is fastened to a large-sized rotor.

Defects such as fatigue cracking or stress corrosion cracking (SCC) caused by long-term operation of the turbine greatly affect safety and early and reliable detection is in demand.

A large-sized blade mounted on a last stage of a large-sized rotor is formed with a base end portion of the large-sized blade having a fork shape, inserted into an outer periphery of a rotor wheel extending having a flange shape from a rotor shaft and is fastened by a pin.

In the turbine blade fastened as above, there is a concern that defects occur in a concentrated manner around a pin hole located on an outermost periphery of the rotor wheel, and reliable test of the position is required.

In a generally performed test having been conducted so far, all the turbine blades are withdrawn from the rotor and surface test technologies such as MT (magnetic particle test) and PT (penetrant test) are applied to each of them in order to ensure test reliability.

However, if such surface test technologies are applied, long time is needed for inspection, and occurrence of new nonconformity caused by disassembling is concerned, which involves not a few demerits.

Thus, a method for testing the turbine blade in a fastened state is proposed (for example, Japanese Patent No. 4694576).

In the prior-art technology in which piezoelectric elements arrayed in plural in a phased array ultrasonic flaw detection sensor are directly brought into contact with a surface portion of a turbine blade still in the fastened state, since most of the surface portion of the turbine blade exposed in the fastened state is curved, a spot with which the sensor can be brought into contact is limited, which is a problem.

Presence of a flat planar portion on the surface of the turbine blade is limited to a tongue portion or the like.

If an incident point of the ultrasound waves is limited to such flat planar portion, a reaching range of the ultrasound waves is largely limited, and the test on the entire region around the above-described pin hole cannot be conducted sufficiently.

Moreover, in the prior-art technology in which a support structure of the plurality of piezoelectric elements transmitting/receiving the ultrasound waves is made flexible and brought into contact with the piezoelectric elements to a curvature portion on the surface of the turbine blade in order to handle the curved shape, a sensor probe having a dedicated structure needs to be produced, and it is difficult to bring such sensor probe into contact with a narrow and small point on the turbine blade, which is also a problem.

SUMMARY OF THE INVENTION

An embodiment of the present invention was made in view of these circumstances, and it is an object of the present invention to enable flaw detection in a state in which the turbine blade is fastened to the rotor.

DETAILED DESCRIPTION OF THE PREFERRED EMBODIMENTS

Prior to explanation of a testing device of a turbine blade according to embodiments of the present invention, a turbine rotor 10 will be explained on the basis of FIGS. 1 to 3.

Figure 1:
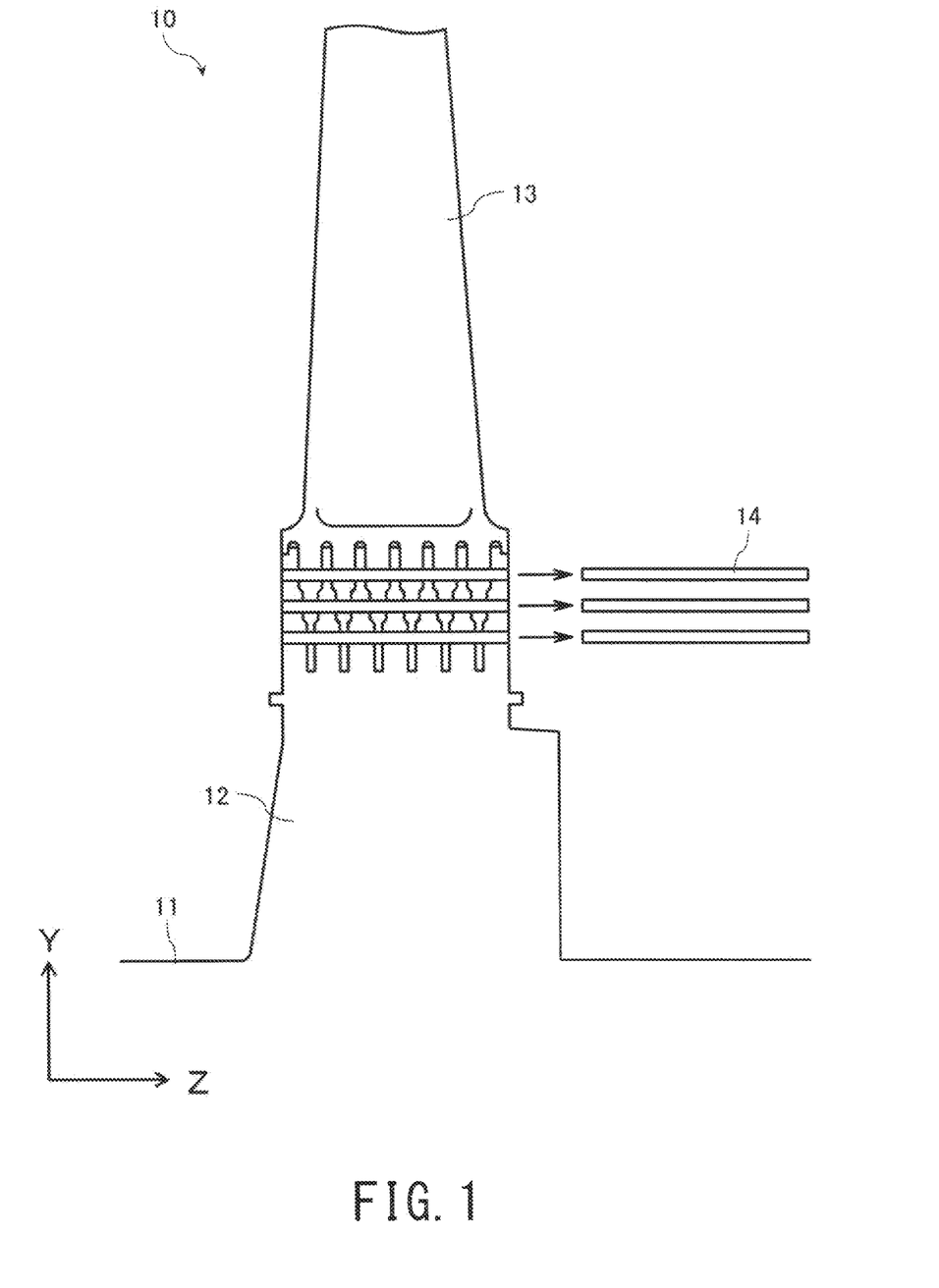
FIG. 1 is a partial sectional view of a turbine rotor.

As illustrated in FIG. 1, in the turbine rotor 10, a rotor wheel 12 extends having a flange shape from a circumferential surface of a shaft 11 rotating around an axis. The rotor wheels 12 are arranged in plural at intervals in an axial direction Z of the shaft 11 (not shown).

Figure 2:
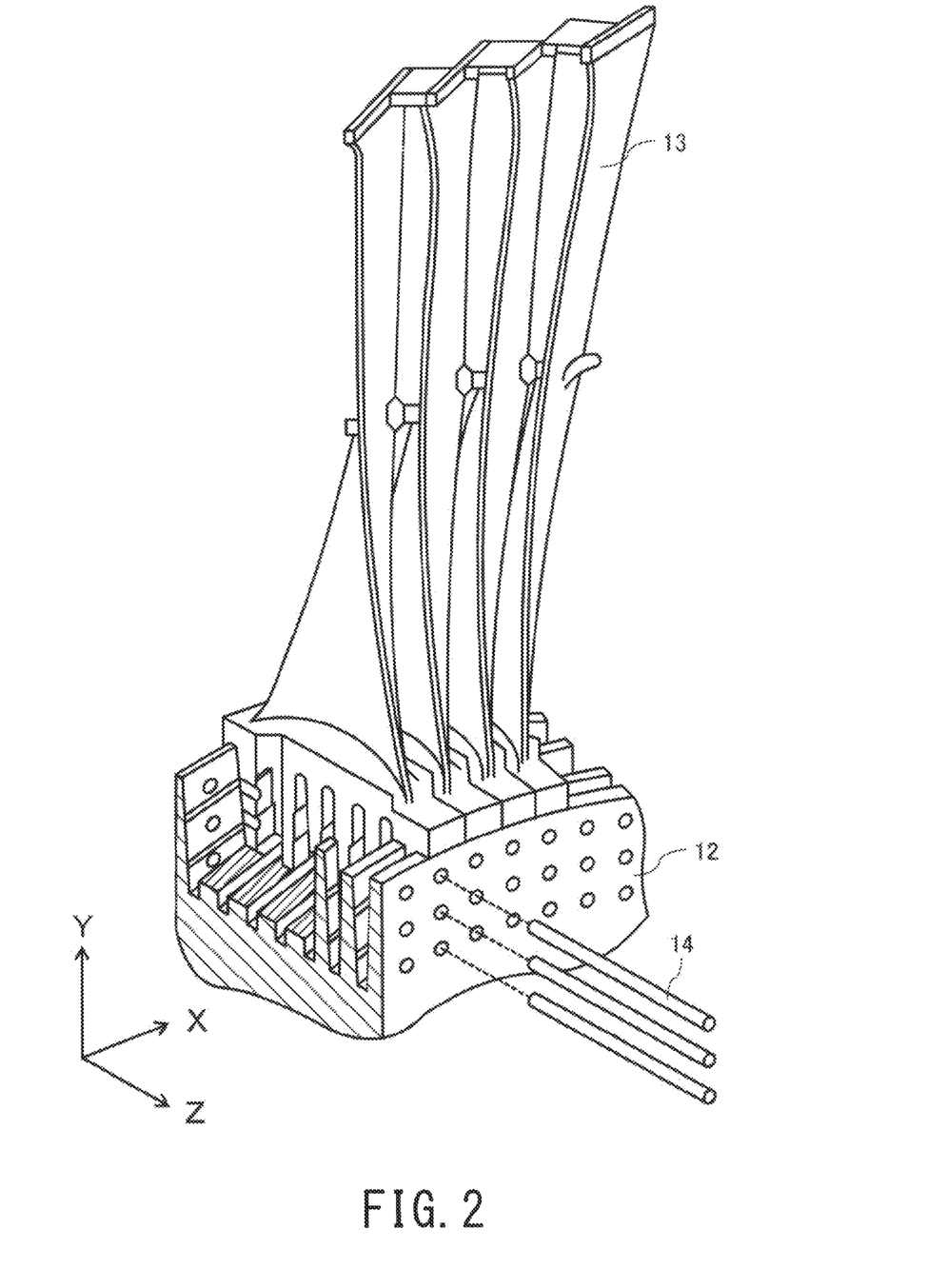
FIG. 2 is a partially notched perspective view illustrating a fastened state between a turbine blade and a turbine wheel.

On an outer periphery of this rotor wheel 12, a plurality of turbine blades 13 are inserted in a radial direction Y and mechanically fastened by pins 14 (see FIG. 2 as appropriate).

As a result, removal of the turbine blade 13 caused by a rotation centrifugal force can be prevented.

In general, a rear stage of the turbine rotor 10 of a low-pressure turbine is designed with a large rotation radius and thus, it receives a large centrifugal load during operation.

As a result, high average stress and local stress are applied to a fastened portion between the rotor wheel 12 and the turbine blade 13, and since it is under an environment of a high-temperature steam, stress corrosion cracking can easily progress.

Figure 3:
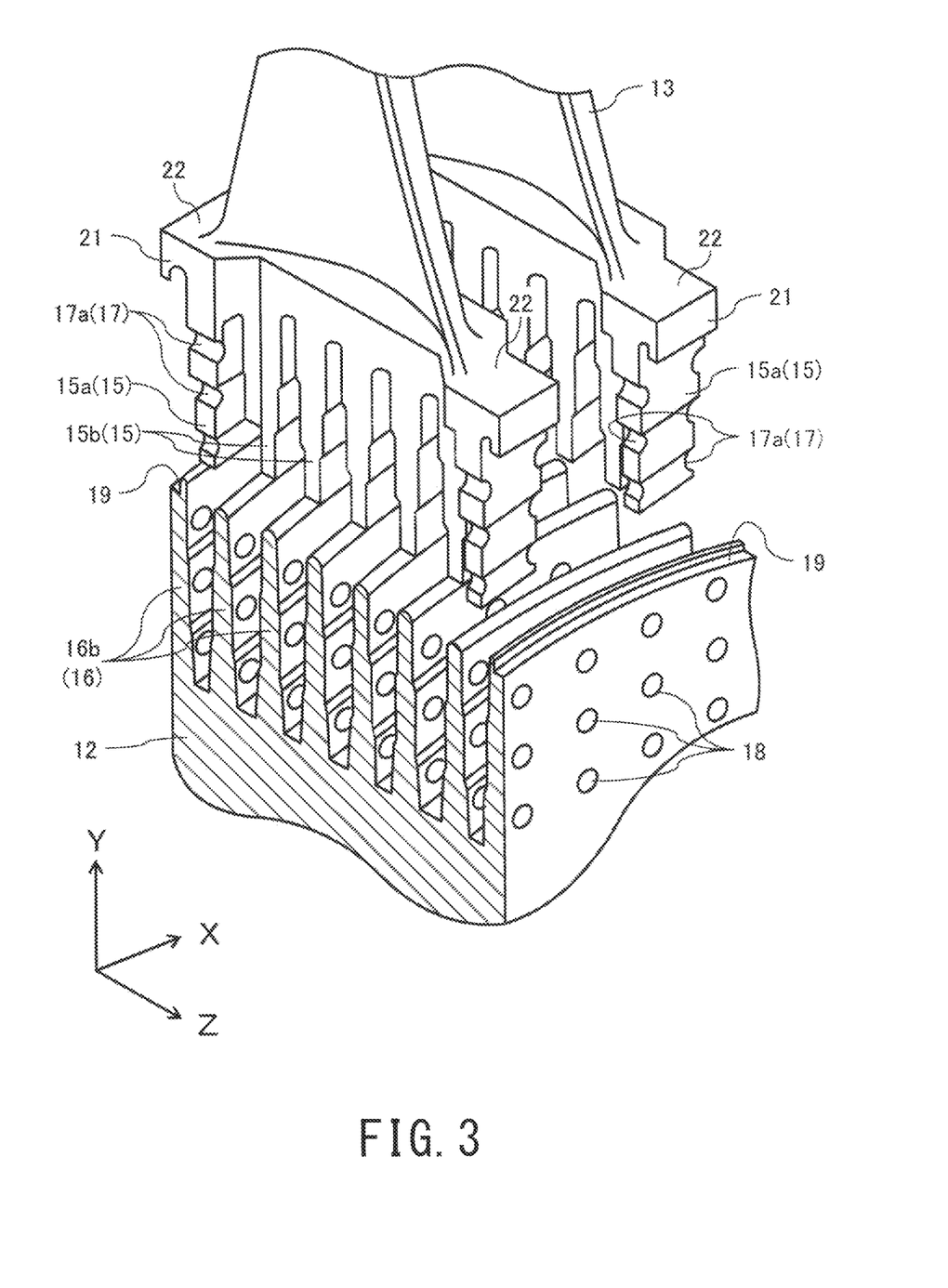
FIG. 3 is a partial enlarged view illustrating a state in which the turbine blade and the turbine wheel are separated.

As illustrated in FIG. 3, a fastening portion 15 is formed at a base end of the turbine blade 13.

Then, on a peripheral edge portion of the rotor wheel 12, a wall 16 forming a groove engaged with the fastening portion 15 of the turbine blade is provided with a distal end directed to the radial direction Y around a periphery.

In the fastening portion 15 of the turbine blade and the wall 16 of the rotor wheel, through holes 17 and 18 for penetration of the pins 14 are provided in a state in which both are engaged with each other.

On the fastening portion 15 of the turbine blade, a plurality of projection portions 15a and 15b each having a fork shape are arrayed in one row in a thickness direction (shaft axis direction Z) of the rotor wheel 12.

The projection portions 15a located on both sides in these projection portions 15a and 15b extend to a circumferential direction of the rotor wheel 12 only by a half pitch with respect to the projection portion 15b located on a center side.

Figure 4A:
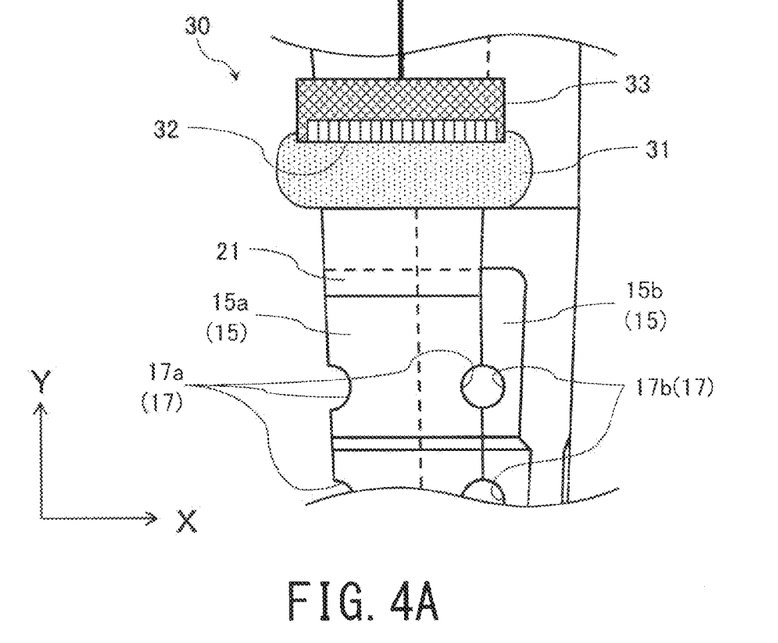
FIGS. 4A and 4B are outline diagrams illustrating an installed state of a test device of a turbine blade according to a first embodiment of the present invention.
Figure 4B:
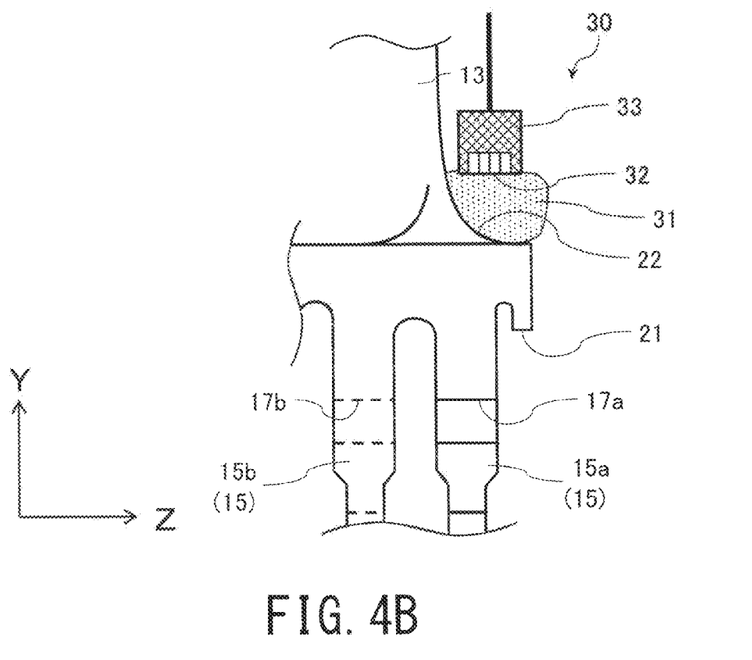

FIG. 4A is an outline view illustrating an installed state of a testing device 30 of the turbine blade from the rotation axis direction Z, and FIG. 4B is an outline view seen from a side surface thereof.

As illustrated in FIG. 4A, semicircular through holes 17a through which pins 14a are to be penetrated are provided so as to form a pair on both side ends of the projection portions 15a on both sides. A circular through hole 17b through which the pin 14 is penetrated is provided at a center of the projection portion 15b on a center side.

As illustrated in FIG. 4B, on a side of a shaft axis direction Z on upper parts of the projection portions 15a on the both sides, a tongue portion 21 engaged with a notch 19 (FIG. 3) on an upper end of an outer wall of the rotor wheel 12 is provided.

A portion whose shape is continuously changed from an upper end surface of the fastening portion 15 of the turbine blade to a rise of a body of the turbine blade is referred to as a platform 22.

This platform 22 has a curved surface structure in which an upper end surface of a tongue portion 21 has a plane but inclination gradually increases toward the body of the turbine blade.

According to the testing device 30 of the turbine blade according to this embodiment, peripheries of semi-circular through holes 17a at the projection portions 15a on the both sides of the fastening portion 15 are main test targets.

First Embodiment

As illustrated in FIG. 4, the testing device 30 of the turbine blade according to a first embodiment (hereinafter referred to simply as "testing device 30") includes a non-compressive elastic medium 31 to be brought into close contact with the platform 22 of the turbine blade 13 in a state fastened to the turbine rotor 10 (FIG. 1), a probe 33 having piezoelectric elements 32 arranged in an array and transmitting ultrasound waves toward the fastening portion 15 of the turbine blade 13 through the elastic medium 31 and receiving echo waves, and a display portion (not shown) for imaging an internal region of the fastening portion 15 on the basis of the echo waves and displaying a defect 35 (FIG. 5) which is present therein.

A matrix array probe in which the piezoelectric elements 32 are two-dimensionally arranged is exemplified as the probe 33, but there is no particular limitation, and general probes for ultrasonic flaw detection are employed.

Here, the piezoelectric element 32 has a piezoelectric effect for reversibly converting the ultrasound waves and an electric signal and is formed of a ceramic, polymeric or composite material.

By oscillating the piezoelectric elements 32 arranged in an array with appropriate time delay added, a transmission direction or a focal position of the ultrasound waves can be controlled.

The ultrasound waves transmitted as above propagate through an inside of the fastening portion 15 of the turbine blade 13 through the elastic medium 31 and if there is a defect such as cracking (including fatigue cracking, stress corrosion cracking, artificial defects such as rectangular, elliptic, and triangular EDM slits and the like) or inclusion, the ultrasound waves are reflected.

The reflected echo waves propagate through the inside of the fastening portion 15 and are received by the piezoelectric element 32 through the elastic medium 31.

A transmission/reception method of the ultrasound waves and echo waves in the probe 33 includes a sector scan type for electronically scanning in a fan shape by varying a flaw detection angle of the ultrasound waves, a linear scan type for electronically scanning in a parallelogram shape by fixing the flaw detection angle of the ultrasound waves, DDF (Dynamic Depth Focusing) by varying a focal depth in conforming to a region to be measured, TOFD (Time of Flight Diffraction) by dividing the piezoelectric element group into those for transmitting ultrasound waves and those for receiving echo waves and the like but they are not particularly limiting and general methods for ultrasonic flaw detection are employed.

The ultrasonic flaw detection method of cracking (defect 35) occurring in the semicircular through hole 17a of the projection portion 15a will be explained on the basis of FIGS. 5 and 6.

Figure 5A:
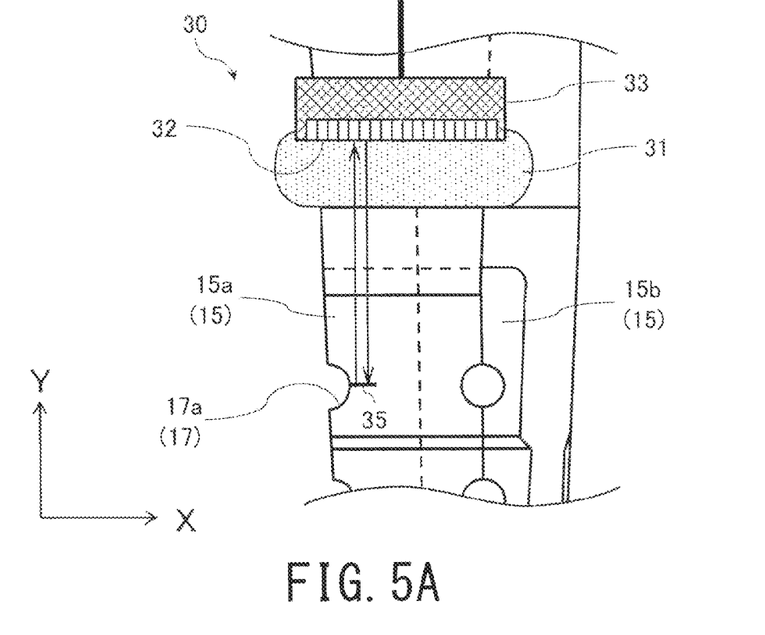
FIGS. 5A and 5B are explanatory views of an ultrasound transmission method of the testing device of the turbine blade according to each of embodiments.

FIG. 5A illustrates a case in which the defect 35 progresses in a direction X perpendicular to a rotor radial direction. In this case, such a method can be employed that common piezoelectric element groups are assigned for transmission of ultrasound waves and for reception of echo waves, and the ultrasound waves are made to enter substantially immediately above the defect 35.

Figure 5B:
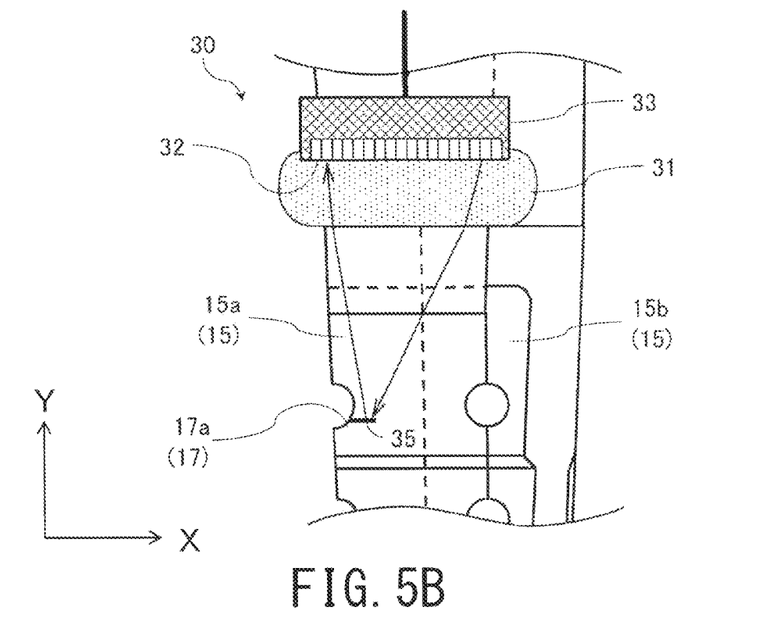

Alternatively, as illustrated in FIG. 5B, if the defect 35 progresses from below the through hole 17a, those for transmission of ultrasound waves are assigned to the piezoelectric element group in a diagonal direction, while those for reception of echo waves are assigned to the piezoelectric element group on an opposite side so that bending angles of the ultrasound waves and the echo waves become large. As a result, detection sensitivity of the defect 35 is improved.

Figure 6A:
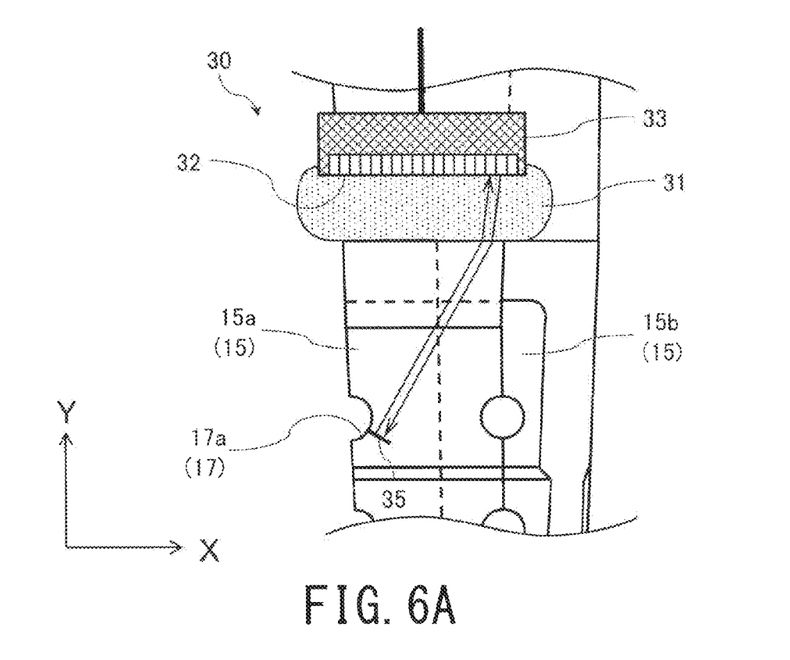
FIGS. 6A and 6B are explanatory views of an ultrasound transmission method of the testing device of the turbine blade according to each of embodiments.

FIG. 6A illustrates a case in which the defect 35 progresses diagonally downward. In this case, the piezoelectric element group present in the diagonal direction is assigned in common for transmission of ultrasound waves and for reception of echo waves, whereby detection sensitivity of the defect 35 can be improved.

Figure 6B:
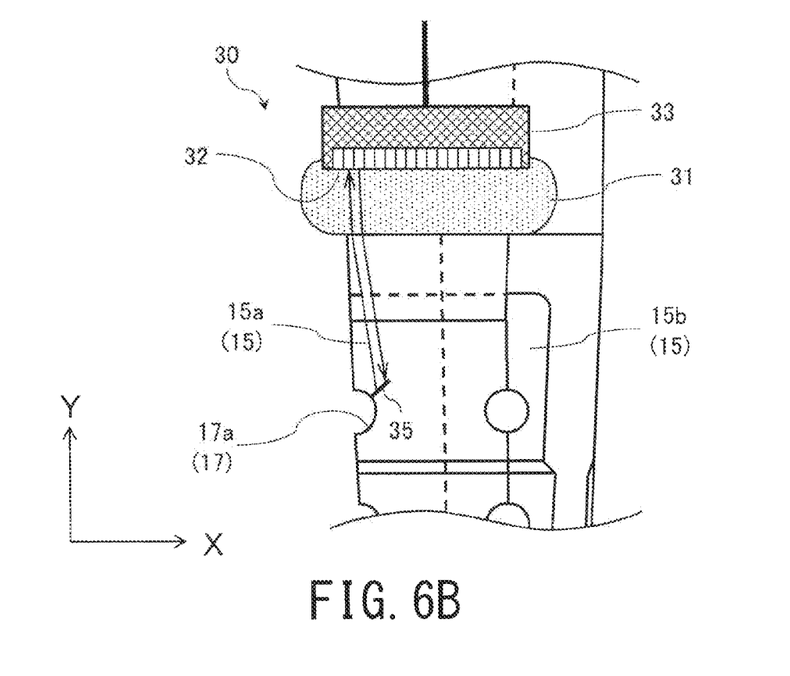

FIG. 6B illustrates a case in which the defect 35 progresses diagonally upward. In this case, the piezoelectric element group present in a radial direction Y is assigned in common for transmission of ultrasound waves and for reception of echo waves, whereby detection sensitivity of the defect 35 can be improved.

As described above, by changing the piezoelectric element group to be assigned for transmission of ultrasound waves and for reception of echo waves, the defect 35 having various positions and progress directions can be detected with high sensitivity.

The elastic medium 31 has non-compressibility, capable of being elastically deformed manually with ease and is to acoustically couple a surface of the probe 33 on a side of the piezoelectric element 32 of the probe 33 and the platform 22 of the turbine blade 13 so that no gap is formed.

Since the elastic medium 31 is non-compressive, it does not change propagation speeds of the ultrasound waves and their echo waves.

As the elastic medium 31, hydrogel, rubber with less ultrasonic damping, konjac and the like can be cited, for example, but the elastic medium 31 is not particularly limited to these examples.

Moreover, the elastic medium 31 is to change the shape to some degree by a pressing force and thus, it is not particularly necessary to form the elastic medium conforming to a shape of a test target.

However, by forming the shape of the elastic medium 31 so as to become a reversed shape of the platform 22 to be brought into close contact, a high close-contact effect can be expected.

In order to improve close contact on respective contact surfaces of the probe 33, the elastic medium 31, and the platform 22, a liquid contact medium may be used as necessary.

Such contact mediums include water, glycerin, machine oil, castor oil and the like can be cited, for example, but not particularly limited, and general mediums for ultrasonic flaw detection with low volatility are employed.

A control portion (not shown) to which the probe 33 is connected through a cable calculates delay time of ultrasound waves transmitted from the respective piezoelectric elements 32 in accordance with curvature of a surface shape of the platform 22 registered in advance.

Then, the ultrasound waves are transmitted from the probe 33 installed at a predetermined position in accordance with this delay time, and the received echo waves are synthesized in accordance with this delay time.

As a result, the internal region of the fastening portion 15 immediately below the platform 22 is imaged, and the defect 35 which is present therein is displayed.

Figure 7:
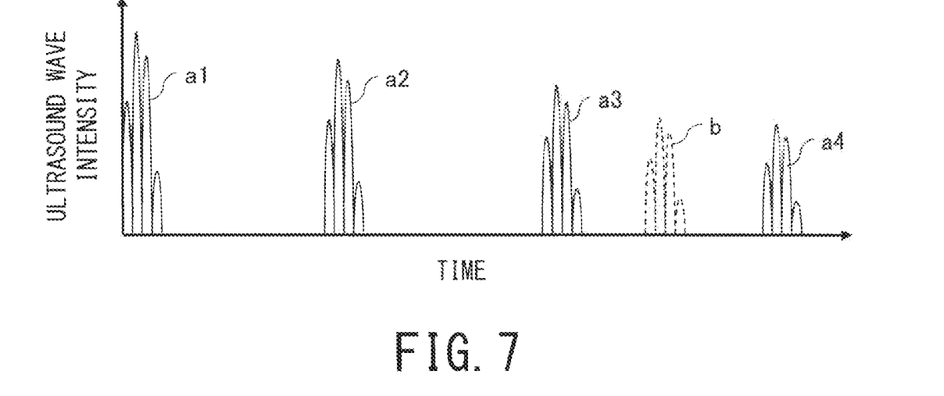
FIG. 7 is a graph of detected echo waves.

A graph in FIG. 7 illustrates the echo waves detected by the control portion (not shown).

When the ultrasonic flaw detection test is to be conducted through the elastic medium 31, a plurality of multiple reflected waves a (a1, a2, a3, a4) from the platform surface reciprocating in the elastic medium 31 might be detected other than echo waves b from the inside of the fastening portion 15 of the turbine blade.

Thus, a thickness or a propagation damping rate of the elastic medium 31 is adjusted so that the multiple reflected waves a generated between the probe 33 and the platform 22 are not superposed on echo waves b from the internal region of the fastening portion 15.

By increasing the propagation damping rate of the elastic medium 31, the multiple reflected waves a can be damped, and superposition on the echo waves b from the internal region of the fastening portion 15 are suppressed.

Alternatively, an ultrasound wave propagation speed ratio between materials of the elastic medium 31 and the turbine blade 13 is calculated, and the thickness of the elastic medium 31 is set so that it deviates from a value obtained by multiplying a distance from the surface of the platform 22 to the through hole 17 by this propagation sped ratio. As a result, superposition of the multiple reflected waves a and the echo waves b can be avoided.

As a result, the defect 35 present inside the fastening portion 15 of the turbine blade can be accurately recognized.

Figure 8:
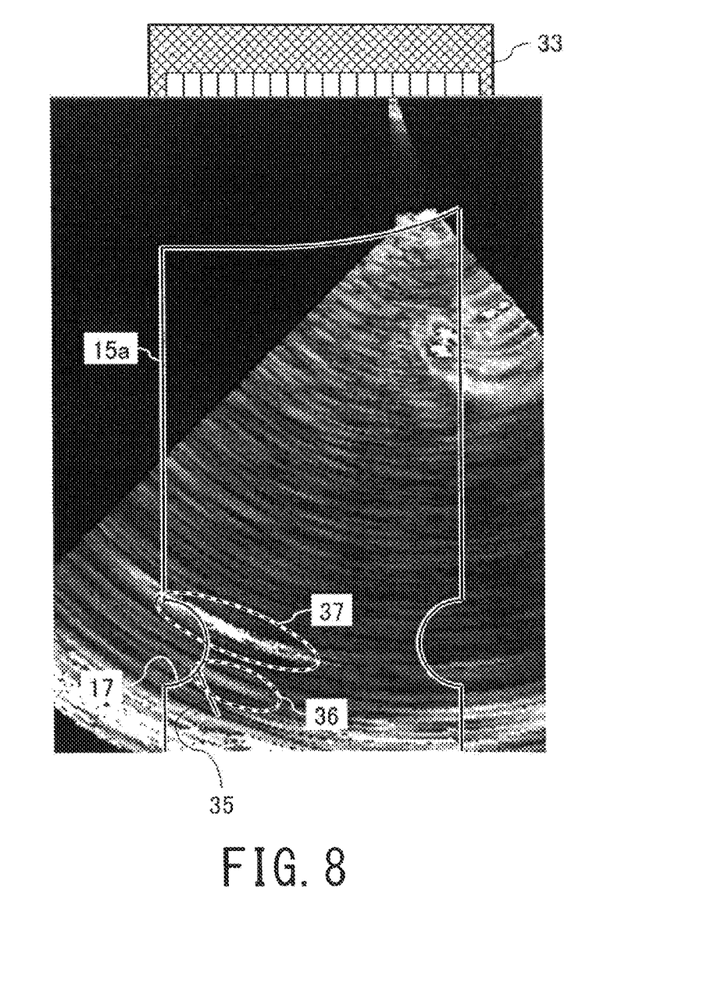
FIG. 8 is a display image of an ultrasound flaw detection result.

FIG. 8 illustrates the internal region of the projection portion 15a imaged on the basis of the echo waves b on the display portion.

An image is a result of sector scan of the projection portion 15a, and a defect echo 36 derived from the defect 35 present therein or an echo 37 derived from the through hole 17 are observed.

As described above, the ultrasound waves can three-dimensionally scan a turbine axis direction, a circumferential direction, and a rotor center direction and thus, flaw detection of a whole region of the internal region of the projection portion 15a is made possible.

Second Embodiment

The testing device 30 of a turbine blade according to a second embodiment will be explained on the basis of FIGS. 9 to 12. In these drawings, portions having configurations or functions common to those in FIG. 4 are indicated by same reference numerals and duplicated explanation will be omitted.

Figure 9:
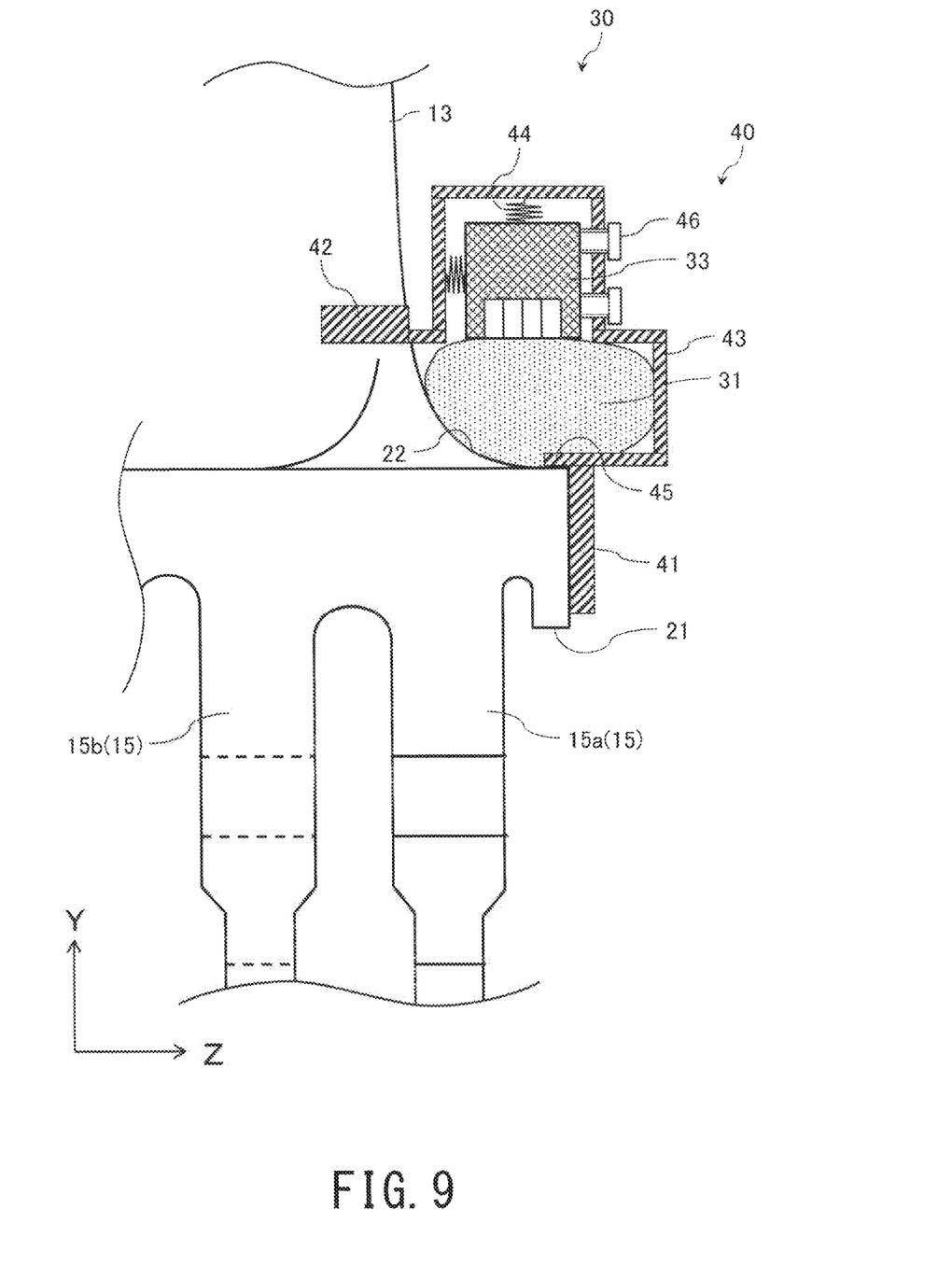
FIG. 9 is a vertical sectional view illustrating the installed state of a testing device of a turbine blade according to a second embodiment of the present invention.

The testing device 30 in the second embodiment further includes a holding portion 40 for holding a state in which the probe 33 is brought into contact with the elastic medium 31 and this elastic medium 31 is in close contact with the platform 22.

This holding portion 40 has an accommodating chamber 43 for accommodating the probe 33 and the elastic medium 31 and bringing the elastic medium 31 into close contact with the platform 22 from an opening portion, a first support member 41 extending in the radial direction Y of the turbine rotor 10 from this accommodating chamber 43 and supporting the turbine blade 13, a second support member 42 extending in the rotation axis direction Z of the turbine rotor 10 from the accommodating chamber 43 and supporting the turbine blade 13, and a position adjustment unit 46 for adjusting a position of the probe 33 in this accommodating chamber 43.

The first support member 41 extends in the radial direction Y of the turbine rotor 10 from the accommodating chamber 43 and supports a surface of the tongue portion 21. This first support member 41 regulates a position of the holding portion 40 in the rotation axis direction Z.

Moreover, on a base end of the first support member 41, a claw-shaped piece 45 extending in a direction of the platform 22 is provided. This claw-shaped piece 45 regulates a position of the holding portion 40 in the radial direction Y.

Figure 10:
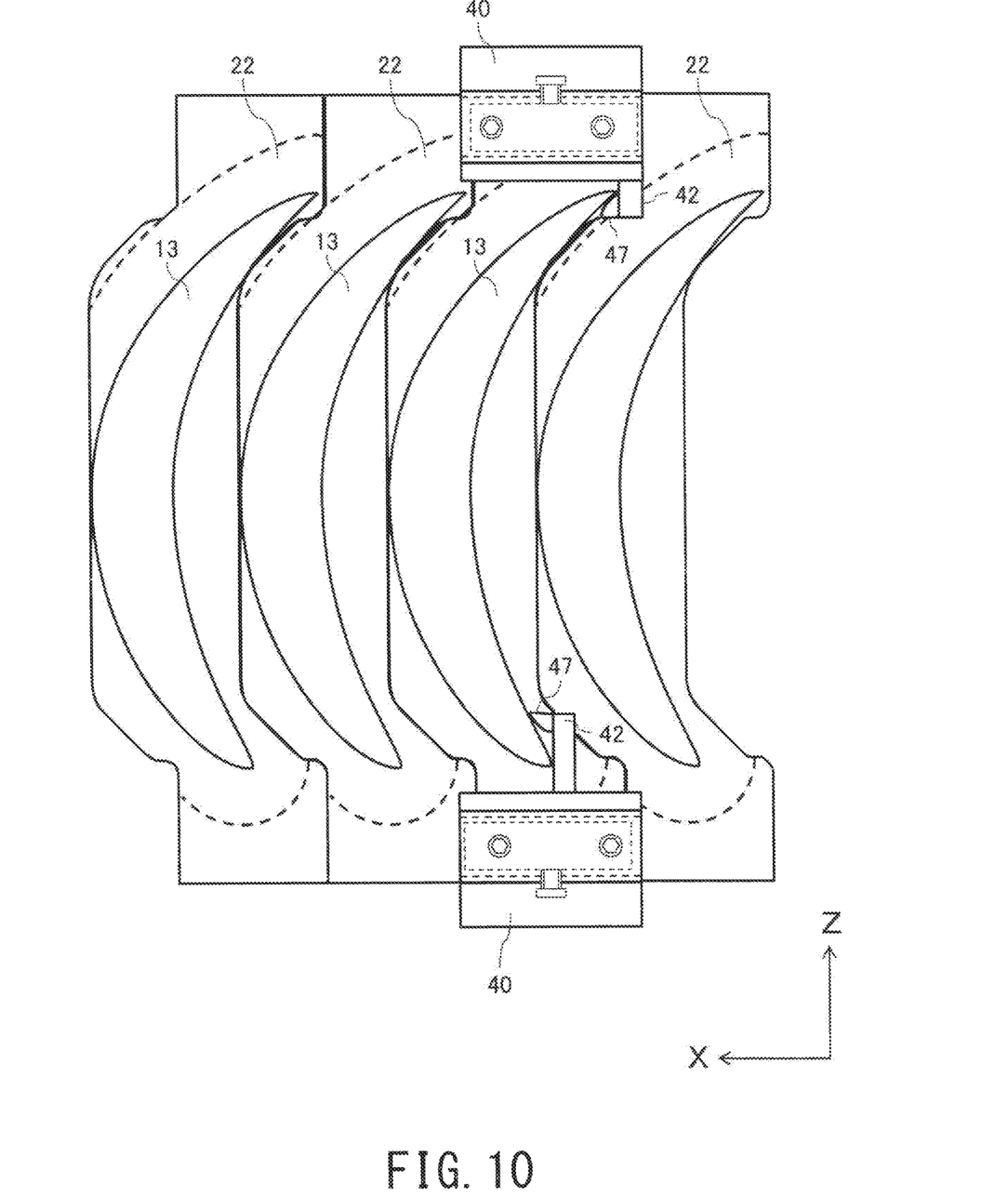
FIG. 10 is a top view illustrating the installed state of the testing device of the turbine blade according to the second embodiment.

The second support member 42 extends in the rotation axis direction Z of the turbine rotor 10 from the accommodating chamber 43 and supports a recessed surface of the turbine blade 13 (see FIG. 10).

This second support member 42 has a claw-shaped piece 47 hooked by a rising portion of the turbine blade 13. Since shapes of the rising portions of the turbine blade 13 are different from a side of a steam inlet and a side of a steam outlet, the second support member 42 needs to be designed conforming to each of them.

The accommodating chamber 43 is provided with the position adjustment unit 46 for adjusting the position of the probe 33 to be accommodated. This position adjustment unit 46 fixes the probe 33 at a predetermined position in collaboration with an urging unit 44. Though not shown, a hole into which a cable to be connected to the probe 33 is inserted is provided in the accommodating chamber 43.

The accommodating chamber 43 is configured such that the elastic medium 31 is in contact with an inner wall of the accommodating chamber 43 except the opening portion where the elastic medium 31 is in close contact with the platform 22 and a portion in contact with the probe 33.

Figure 11A:
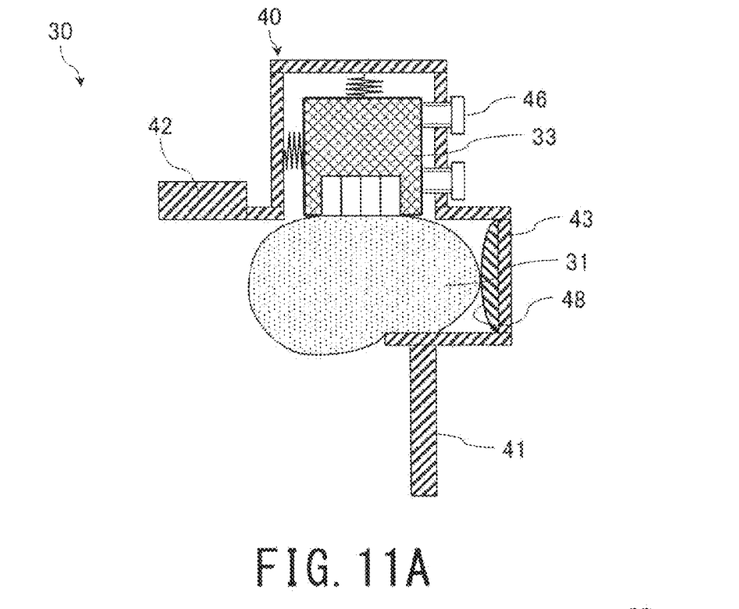
FIGS. 11A and 11B are explanatory views of an installation method of the testing device of the turbine blade according to the second embodiment.
Figure 11B:
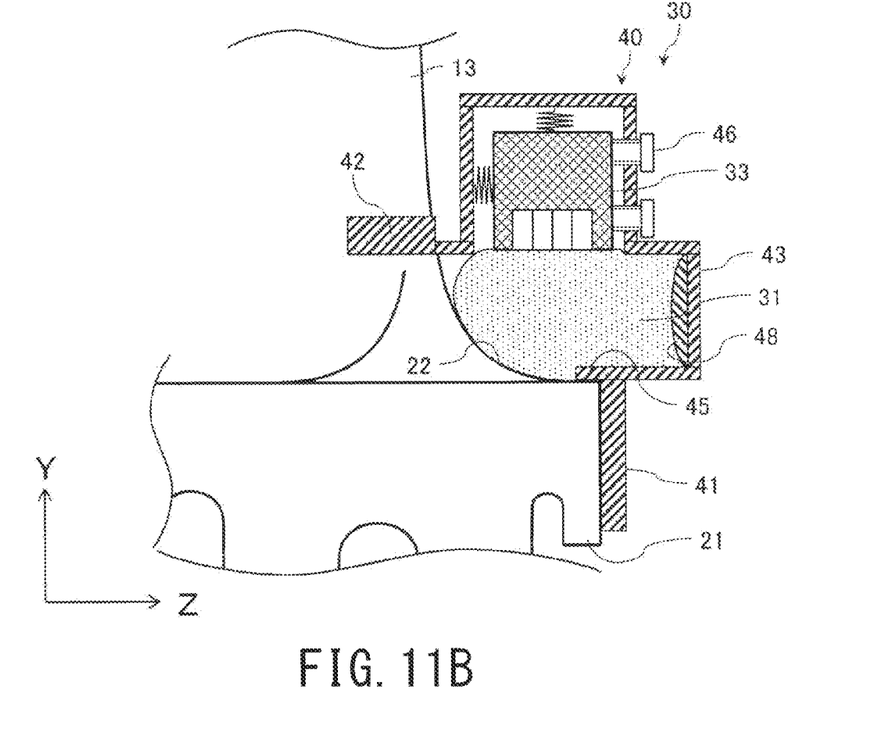

As illustrated in FIG. 11, a relief member 48 might be provided on the inner wall of this accommodating chamber 43 so that the elastic medium 31 is in uniform contact with the inner wall of the accommodating chamber 43.

An installing method of the testing device 30 held by the holding portion 40 will be explained on the basis of FIG. 11.

As illustrated in FIG. 11A, the position of the probe 33 is adjusted as appropriate, and the elastic medium 31 is accommodated in the accommodating chamber 43.

First, the recessed surface of the turbine blade 13 is supported by the second support member 42 and made a first reference point, and a circumferential position is determined. Subsequently, the first support member 41 is pressed onto a corner surface of the tongue portion 21, and positions of the radial direction Y and the rotation axis direction Z are determined (FIG. 11B).

The elastic medium 31 needs to fill an ultrasound propagation path between the probe 33 and the platform 22 without a gap.

Moreover, since the elastic medium 31 is non-compressive, it preferably has such a size that an excess volume does not overflow from an internal volume of the accommodating chamber 43 in a state in which the holding portion 40 is installed on the turbine blade 13.

Figures 12A, 12B, 12C:
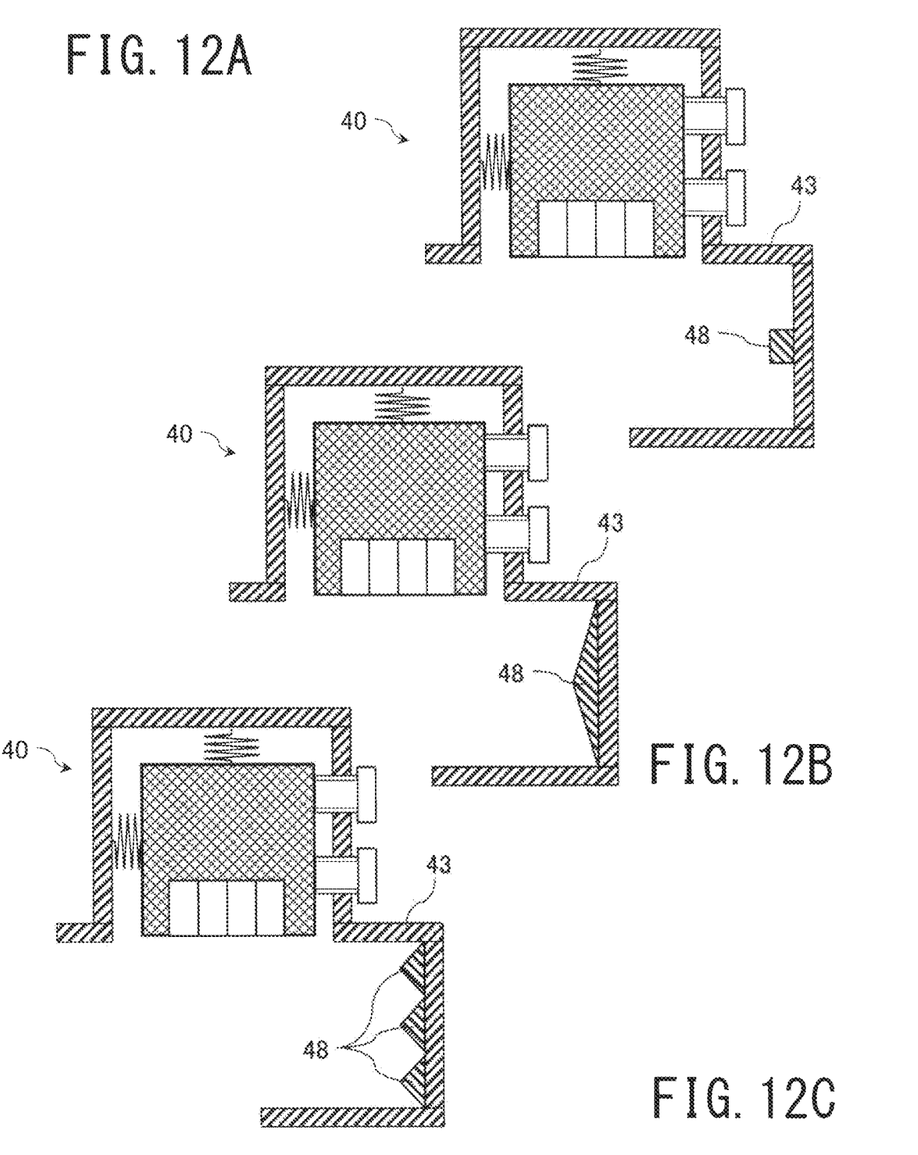
FIGS. 12A, 12B, and 12C are vertical sectional views illustrating a variation of the testing device of the turbine blade according to the second embodiment.

FIG. 12 illustrates a variation of a shape of the relief member 48.

In FIG. 11, the shape of the relief member 48 is elliptic, but as illustrated in FIGS. 12A, 12B, and 12C, the shape of the relief member 48 may be rectangular, triangular, or wavy.

The shape of the relief member 48 is not particularly limited as long as the elastic medium 31 pushed out into an inside of the accommodating chamber 43 is filled without overflow or a gap when the holding portion 40 is attached to the turbine blade 13.

By employing the holding portion 40 as above, the testing device 30 can be installed and positioned with good reproducibility with respect to a large number of turbine blades 13 provided radially in the circumferential direction of the rotor wheel 12.

Third Embodiment

Figure 13A:
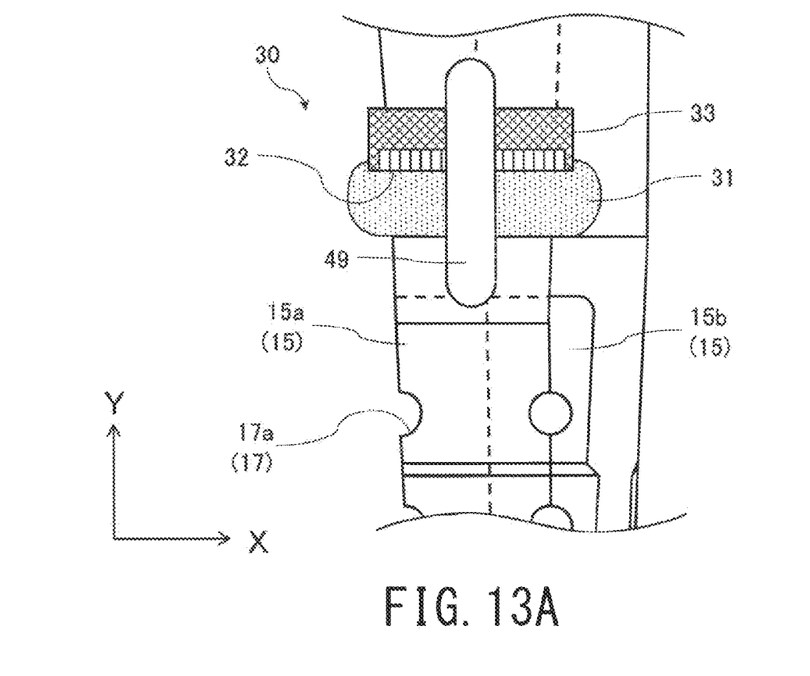
FIGS. 13A and 13B are outline views illustrating an installed state of a testing device of a turbine blade according to a third embodiment of the present invention.
Figure 13B:
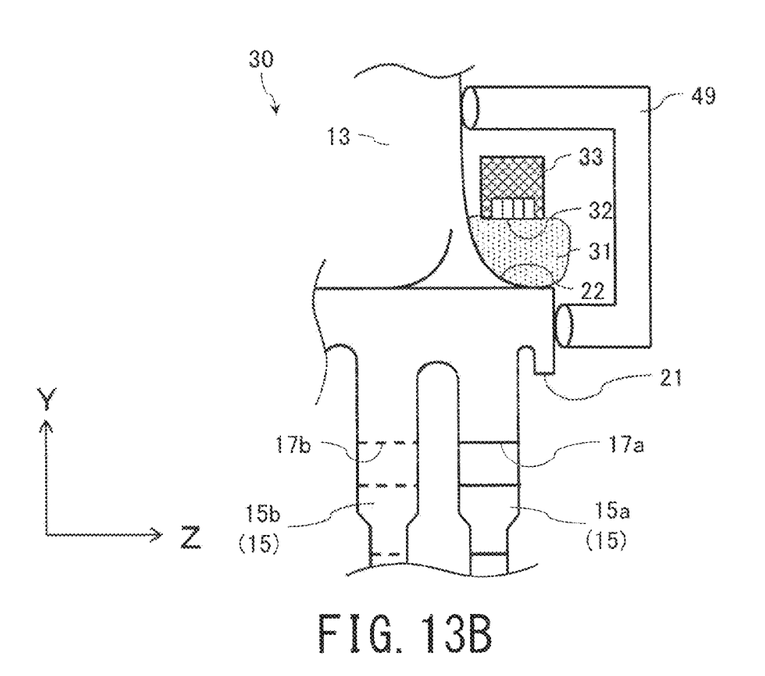

The testing device 30 of a turbine blade according to a third embodiment will be explained on the basis of FIGS. 13A and 13B.

The testing device 30 of a turbine blade according to the third embodiment further includes a magnetizing unit 49 for magnetizing a magnetic body, and the elastic medium 31 is mixed with magnetic particles.

In these drawings, portions having configurations or functions common to those in FIG. 4 are indicated by same reference numerals and duplicated explanation will be omitted.

The magnetic body particles to be mixed in the elastic medium 31 include iron particles and the like but those magnetized by the magnetizing unit 49 can be used as appropriate.

Concentration of the magnetic body particles to be mixed shall be such a degree that elasticity of the elastic medium 31 is not lost and its grain size shall be such that the particles do not become a scattering source of the ultrasound waves.

The magnetizing unit 49 is realized by an electromagnet or a permanent magnet.

By arranging both poles of the magnetizing unit 49 at positions sandwiching the elastic medium 31, the turbine blade 13 and the elastic medium 31 can be both magnetized, and close contact between the both can be improved.

The magnetizing unit 49 may be provided on the holding portion 40 (FIG. 9), and a part of or the whole of the holding portion 40 may be constituted by a magnetic body.

Figure 14:
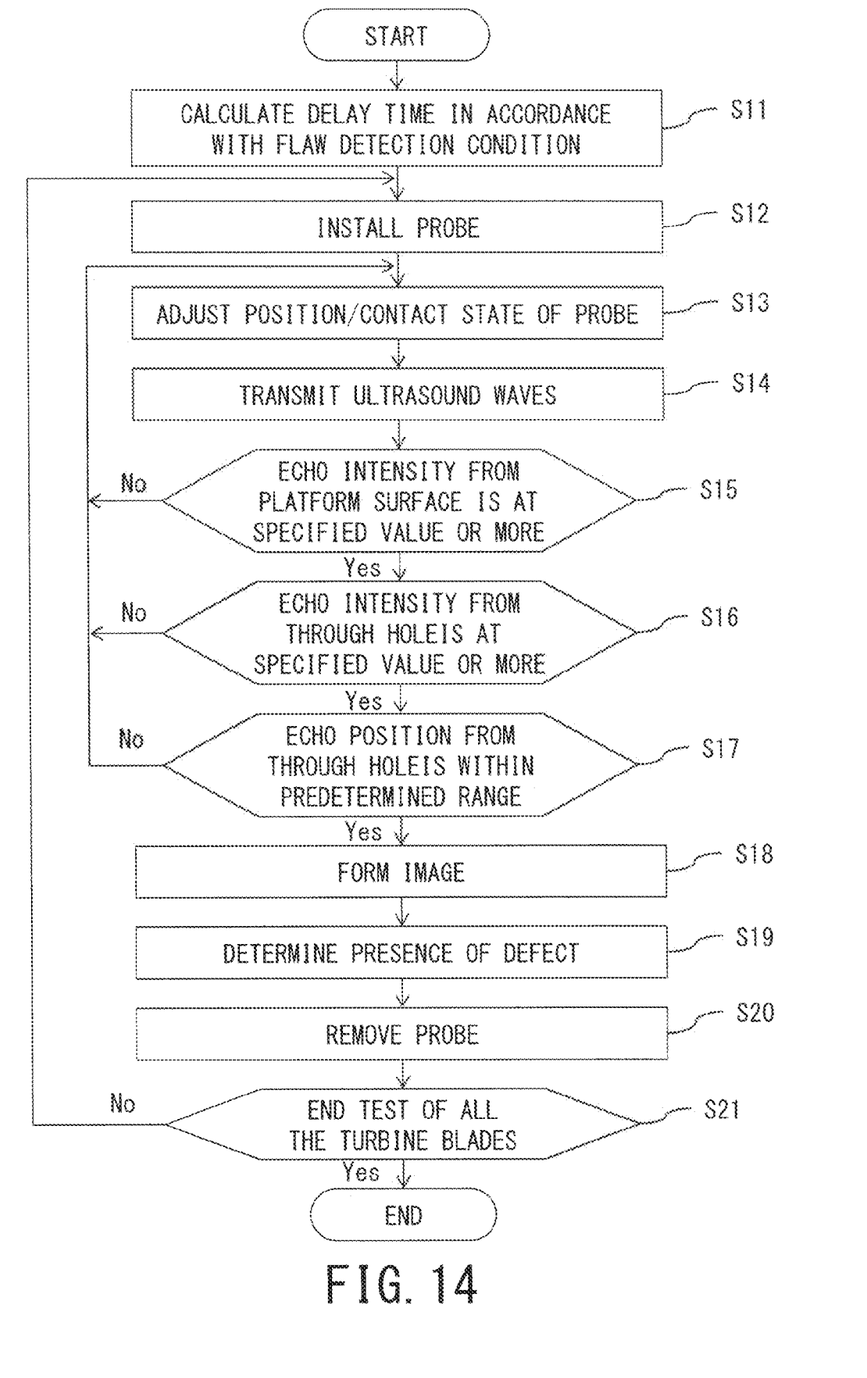
FIG. 14 is a flowchart for explaining an operation of the testing device of the turbine blade according to each of the embodiments.

A testing method of the turbine blade according to each of the embodiments will be explained on the basis of a flowchart in FIG. 14. First, oscillation timing (delay time) of each of the piezoelectric elements 32 is calculated in accordance with a flaw detection condition (S11). The probe 33 is installed on the platform 22 of the turbine blade while sandwiching the elastic medium 31, positions are adjusted, and ultrasound waves are transmitted (S12, S13, S14).

If at least either one of echo intensity from the platform surface and echo intensity from the through hole 17 has not reached a specified value (S15, S16: No), detection sensitivity of a defect echo is low and defective contact of the elastic medium 31, the probe 33, and the platform 22 is suspected and thus, a contact state among them is adjusted again (S13).

Moreover, if a position of the echo from the through hole 17 is not within a predetermined range (S17: No), there is a concern that a set position of the probe 33 is shifted, and thus, positioning adjustment is made again (S13). Alternatively, delay time may be adjusted.

When the specified value of the echo intensity and the range of the echo position satisfy predetermined conditions (S15, S16, S17: Yes), an image of the internal region of the fastening portion 15 is formed on the basis of the echo waves (S18). Then, it is determined whether or not the defect 35 is present in this image (S19).

Then, the probe 33 is removed (S20) and is installed on the platform 22 of the subsequent turbine blade and the above-described work is repeated (S21; No), and the test for all the turbine blades in the state fastened to the turbine rotor is finished (S21; Yes END).

According to the testing device of the turbine blade of at least one embodiment described above, by installing the probe on the platform of the turbine blade through the elastic medium, a flaw detection test can be made easily in a state in which the fastening portion with the rotor is fastened by making the ultrasound waves enter the curvature surface of the turbine blade.

Some embodiments of the present invention are explained but these embodiments are presented as examples and are not intended to limit a scope of the invention. These embodiments can be put into practice in other various forms and capable of various omission, replacement, changes and combinations within a range not departing from a gist of the invention. These embodiments and their variations are included in the scope and the gist of the invention and also included in a scope of the invention described in claims and its equivalents.

What is claimed is:

1. A testing device of a turbine blade comprising:
   an elastic medium configured to contact with a platform of the turbine blade in a state fastened to a turbine rotor;
   a probe, comprising piezoelectric elements arranged in an array, configured to transmit ultrasound waves toward a fastening portion of the turbine blade through the elastic medium contacting with the platform and to receive echo waves of the ultrasound waves; an accommodating chamber configured to accommodate the probe and the elastic medium and further configured to hold the probe contacting with the elastic medium that is in contact with the platform; and
   a display configured to image an internal region of the fastening portion on the basis of the echo waves, wherein the accommodating chamber comprises:
   an opening from which the elastic medium is configured to contact with the platform;
   a first support, extending in a radial direction of the turbine rotor, configured to abut with the turbine blade;
   a second support, extending in a rotation axis direction of the turbine rotor, configured to abut with the turbine blade; and
   a position adjuster configured to adjust a position of the probe in the accommodating chamber.

2. The testing device of a turbine blade according to claim 1, wherein
   the elastic medium has a reversed shape of the platform to be brought into close contact.

3. The testing device of a turbine blade according to claim 1,
   wherein
   the elastic medium is mixed with magnetic body particles.

4. The testing device of a turbine blade according to claim 1, wherein:
   a thickness or a propagation damping rate of the elastic medium is set in order to prevent multiple reflected waves generated between the probe and the platform from being superposed on echo waves from a region including the fastening portion.

5. A testing method of a turbine blade, comprising
   preparing a probe, an elastic medium, and an accommodating chamber, the accommodating chamber comprising:
   an opening;
   a first support extending in a radial direction of the turbine rotor;
   a second support extending in a rotation axis direction of the turbine rotor,
   accommodating the probe and the elastic medium in the accommodating chamber so that the elastic medium is placed adjacent to the opening;
   abutting the first and the second support with the turbine rotor so that the elastic medium contacts with a platform of the turbine blade in a state fastened to a turbine rotor through the opening;
   transmitting ultrasound waves from a probe toward a fastening portion of the turbine blade through the elastic medium;
   receiving echo waves of the transmitted ultrasound waves by the probe; and
   imaging an internal region of the fastening portion on the basis of the echo waves.

6. The testing method of a turbine blade according to claim 5, further comprising:
   adjusting a position of the probe in the accommodating chamber.

* * * * *